United States Patent [19]

Miller et al.

[11] Patent Number: 5,773,279
[45] Date of Patent: Jun. 30, 1998

[54] CULTURE MEDIUM AND METHOD FOR REPAIR OF MICROBIAL CELLS

[75] Inventors: Raymond L. Miller, Lindenwold; Martin R. Gould; Sudhakar Vulimiri, both of Gibbstown, all of N.J.

[73] Assignee: Neogen Corporation, Lansing, Mich.

[21] Appl. No.: 753,715

[22] Filed: Nov. 27, 1996

[51] Int. Cl.⁶ .............................. C12N 1/00; C12N 1/04; C12N 1/20

[52] U.S. Cl. .................. 435/243; 435/252.1; 435/253.6; 435/260

[58] Field of Search ................................ 435/243, 252.1, 435/253.6, 260

[56] References Cited

U.S. PATENT DOCUMENTS

| | | | |
|---|---|---|---|
| 2,770,574 | 11/1956 | Stokes et al. | 435/252.8 |
| 2,792,331 | 5/1957 | Boxell | 435/253.6 |
| 3,987,207 | 10/1976 | Spaeti et al. | 426/99 |
| 4,822,490 | 4/1989 | Dyadechko et al. | 210/611 |
| 5,098,832 | 3/1992 | Rambach | 435/34 |
| 5,145,786 | 9/1992 | Bailey et al. | 435/252.4 |
| 5,296,370 | 3/1994 | Martin et al. | 435/252.1 |

FOREIGN PATENT DOCUMENTS

| | | |
|---|---|---|
| 62-236477 | 10/1987 | Japan. |
| 08252087 | 10/1996 | Japan. |

OTHER PUBLICATIONS

Atlas, R. Handbook of Microbiological Media, pp. 1–2, 1993.

Buchanan et al. Bergey's Manual of Determinative Bacteriology, 8th ed. pp. 294 and 485, 1973.

*Primary Examiner*—Leon B. Lankford, Jr.
*Assistant Examiner*—Christopher R. Tate
*Attorney, Agent, or Firm*—Ian C. McLeod

[57] ABSTRACT

A dry, powdered culture medium for use in repair of microbial cells is described. The method involves combining fatty acids, an emulsifier and a carbon source to form a powder which is then mixed with a nutrient medium, yeast extract, an antioxidant and a buffering salt as a dry powder. Preferably the ingredients are milled together.

6 Claims, No Drawings

CULTURE MEDIUM AND METHOD FOR REPAIR OF MICROBIAL CELLS

BACKGROUND OF THE INVENTION

(1) Summary of the Invention

The present invention relates to a powdered, dry culture medium which can be added to water and used to repair injured microbial cells, particularly disease microbes which are to be detected in foods, particularly processed foods where the cells can be injured and yet still have produced lethal toxins. In particular, the present invention provides the necessary ingredients in an effective form which allows shipment prior to use without having to transport water.

(2) Description of Related Art

U.S. Pat. No. 5,296,370 to Martin et al describes a very effective liquid culture medium for membrane repair of microbial cells, the disclosure of which is incorporated by reference. In this invention, the culture medium contains a non-selective complete medium to supply nutrients required by food pathogens, a yeast derivative, one or more antioxidants, an oxygen tension reducing agent and one or more fatty acids for membrane repair. The fatty acids are 10 to 25 carbon atoms in length and can have up to 4 double bonds and are used in amounts between 0.025 and 1.0 weight percent. The complete medium can include tryptic soy broth, nutrient broth, Eagles medium or yeast mold broth in an amount between about 2.5 and 20 weight percent. The antioxidants can include pyruvate, succinate, glutathione, catalase, selenium, albumin, glucose, BHA, BHT, ascorbic acid, lactic acid, uric acid, superoxide dismutase, glutathione peroxidase acid and n-acetyl cysteine, vitamin E and beta-carotine in amounts of about 0.10 to 1.0 percent by weight. The yeast derivative can be yeast extract, live yeast cell derivative, autolysed yeast, enzymatically treated yeast and mixtures thereof in amounts between about 0.1 and 1.0 weight percent. Various protein supplements such as casamino acids, brain-heart infusion proteins, proteases, peptones and mixtures thereof can be used in about between about 0.1 and 1.0 weight percent. Various preferred liquid media are described.

Other prior art relating to culture media is described in U.S. Pat. No. 2,792,331 to Boxell (skin and joint components); U.S. Pat. No. 2,770,574 to Stokes et al (yeast extract mannitol buffer, peptone, selenite for Salmonella); U.S. Pat. No. 4,822,490 to Dyadechko et al (water soluble buffers for Pseudomonas); U.S. Pat. No. 5,098,832 to Rambach (polyol for Salmonella); U.S. Pat. No. 5,145,786 to Bailey et al (pre-enrichment broth for Salmonella using buffers). All of this prior art is concerned with forming liquid broths.

The problem is that the prior art culture media involving the use of fatty acids are not designed to be provided as a dry powder. The fatty acids, such as chicken fat are liquid and not easily properly included in a dry culture medium as a single formulation. Sterilization is difficult to achieve.

OBJECTS

It is therefore an object of the present invention to provide an improved dry, single formulation culture medium which can be used for repair of microbial cells. It is further an object of the present invention to provide a single formulation culture medium which is easily sterilized. Further, it is an object of the present invention to provide a culture medium which is economical to prepare. These and other objects will become increasingly apparent by reference to the following description.

DESCRIPTION OF PREFERRED EMBODIMENTS

The present invention relates to a heterogenous culture medium for repair of microbial cells which comprises a powdered mixture of:

(A) a mixture of a nutrient medium for the microbial cells, a yeast derivative, an antioxidant, and a buffering salt which forms a dry powder; and (B) a mixture of a fatty acid required for membrane repair and emulsifier for the fatty acid and a carbon source for the microbial cells which forms a dry powder, wherein each of the ingredients is present in amounts which promote the repair.

Further the present invention relates to a heterogeneous culture medium for repair of microbial cells which comprises as a powdered mixture ingredients:

(A) a milled mixture of a nutrient medium for the microbial cells, yeast extract as a yeast derivative, pyruvate and thioglycolate as antioxidants, potassium dihydrogen phosphate and sodium hydrogen phosphate as buffering salts which forms a dry powder; and (B) a milled mixture of chicken fat, polyoxyethylene (20) sorbitan mono-oleate as an emulsifier for the chicken fat and mannitol as a carbon source for the microbial cells which forms a dried powder, wherein each of the ingredients is present in amounts which promote the repair.

The present invention also relates to a method for repairing of microbial cells which comprises:

(a) providing a heterogenous culture medium for repair of microbial cells which comprises a powdered mixture of:

(A) a mixture of a nutrient medium for the microbial cells a yeast derivative, an antioxidant, and a buffering salt which forms a dry powder; and (B) a mixture of a fatty acid required for membrane repair and emulsifier for the fatty acid and a carbon source for the microbial cells which forms a dry powder, wherein each of the ingredients is present in amounts which promote the repair;

(b) mixing the powdered mixture with water to provide a liquid culture medium;

(c) providing the microbial cells in the liquid culture medium;

(d) culturing the cells in the liquid culture medium until the cells are repaired.

The present invention also relates to a method for repairing microbial cells which comprises:

(a) providing a heterogeneous culture medium for repair of microbial cells which comprises as a powdered mixture ingredients (A) a milled mixture of a nutrient medium for the microbial cells, yeast extract as a yeast derivative, pyruvate and thioglycolate as antioxidants potassium dihydrogen phosphate and sodium hydrogen phosphate as buffering salts which forms a dry powder; and (B) a milled mixture of chicken fat, polyoxyethylene (20) sorbitan mono-oleate as an emulsifier and mannitol as a carbon source for the microbial cells which forms a dried powder, wherein each of the ingredients is present in amounts which promote the repair;

(b) mixing the powdered mixture with water to provide a liquid culture medium;

(c) providing the microbial cells in the liquid culture medium; and (d) culturing the cells in the culture medium until the cells are repaired.

The preferred culture medium includes a method for preparing a heterogenous culture medium for microbial cells which comprises:

(a) mixing a purified mixture of:

(A) a mixture of a nutrient medium for the microbial cells, a yeast derivative, an antioxidant, and a buffering salt which forms a dry powder; and (B) a mixture of a fatty acid required for membrane repair and emulsifier for the fatty acid and a carbon source for the microbial cells which forms a dry powder, wherein each of the ingredients is present in amounts which promote the repair; and (b) packaging the mixture.

The present invention also relates to a method for preparing a heterogenous culture medium for microbial cells which comprises:

(a) mixing a powdered mixture of:

(A) a milled mixture of a nutrient medium for the microbial cells, yeast extract as a yeast derivative, pyruvate and thioglycolate as antioxidants, potassium dihydrogen phosphate and sodium hydrogen phosphate as buffering salts which forms a dry powder; and (B) a milled mixture of chicken fat, polyoxyethylene (20) sorbitan mono-oleate as an emulsifier for the chicken fat and mannitol as a carbon source for the microbial cells which forms a dried powder, wherein each of the ingredients is present in amounts which promote the repair; and (b) packaging the mixture.

The preferred ranges are: for the nutrient medium between 1 and 90 parts per part of (A) together; the yeast derivative between about 1 and 50 per part of (A) together between about 1 and 90 part of buffering salts per part of (A) together; between about 0.1 and 50 part of fatty acid per part of (B) together, between 0.1 and 50 part of an emulsifier for the fatty acid per part of (B) together and between about 1 and 90 part of the carbon source per part of B together, all by weight.

The present invention thus relates to a method by which a patented complex microbiological resuscitation medium is formulated into a dry mixture, suitable for sterilization by irradiation, extended shelf life at wide range of temperatures and rehydration for use thereafter. In the method, the fatty acid (lipid), such as chicken fat, is added evenly to a dry media mix rather than as a liquid. Buffering phosphates which permits a greater range of microbial repair metabolism and an assimilable carbohydrate provides better metabolism.

The resuscitation medium of U.S. Pat. No. 5,296,370 to Martin et al is always prepared in liquid form and sterilized by filtration or autoclaving which is difficult for a manufacturer as well as customers which use the formulation. For example:

(1) the culture medium is contained in large (usually 500 ml) bottles;

(2) if not autoclaved, then "sterile filling" into sterilized bottles is required;

(3) if autoclaved, then compositional analysis of each lot is required for measurement of any individual reagent changes;

(4) there is a significant cost of shipping and storage at producer's site and user's site because of the bulk of the liquid; and (5) there is a greater susceptibility to contaminants and growth during storage and preuse.

The present invention permits bulk formulation of a complex dry mix, including a semi-solid fat, complete with even dispersal of all ingredients, subsequent aliquoting to small bottles or other containers for easy sterilization by irradiation, storage at room temperature, inexpensive shipping alone or within bacterial test kits. Further, the added carbohydrate encourages commencement of energy production by cells and therefore helpful in their repairs made possible by the remaining medium ingredients. Further, the use of an emulsifier (Tween 80) to obtain incorporation of the preferred fat into the medium, is believed to aid in the use of the fat intracellularly.

EXAMPLE 1

The preferred ingredients of the formulation of the present invention are set forth in TABLE 1.

TABLE 1

| | Ingredients | | U.S. Pat. No. 5,296,370 | | Improved Medium | |
|---|---|---|---|---|---|---|
| | Name | Source | Wt. % | g/L | g/L | Wt. % |
| Nutrient Medium | Tryptic soy broth | EMS (Gibbstown, NJ) | 3% | 30.0 | 15.00 | 1.5 |
| Yeast derivative | Yeast extract | Difco or BBL (Detroit, MI) | 0.5% | 5.0 | 2.50 | 0.25 |
| Antioxidant | Sodium pyruvate | Sigma (St. Louis, MO) | 0.25% | 2.5 | 1.25 | 0.125 |
| Oxygen Tension | Sodium thioglycolate | Sigma (St. Louis, MO) | 0.01% | 0.1 | 0.05 | 0005 |
| Fatty acid | Chicken fat | Capital City (Monett, MO) | 0.1% | 1.0 | 0.50 | 005 |
| Buffer | $KH_2PO_4$ | Fisher (Itasca, IL) | — | | 2.50 | 0.25 |
| Buffer | $Na_2HPO_4$ | Fisher (Itasca, IL) | — | | 7.50 | 0.75 |
| Carbon Source | Mannitol | Fisher (Itasca, IL) | — | | 5.00 | 0.5 |

TABLE 1-continued

|  | Ingredients | U.S. Pat. No. 5,296,370 | | Improved Medium | |
|---|---|---|---|---|---|
| Name | Source | Wt. % | g/L | g/L | Wt. % |
| Emulsifier | Tween 80 | 0.3% | 3.0 | 1.50 | 0.15 |
|  | TOTALS | 4.1% |  |  | 4.085% |

The medium was prepared from ingredients as set forth in the following Table 2.

TABLE 2

| Amount Required to Make 1 L | List of Materials |
|---|---|
| 15.0 g | CASO (E.M. Science ⊆ to Tryptic Soy (Broth) |
| 2.5 g | Yeast Extract |
| 1.25 g | Sodium Pyruvate |
| 0.05 g | Sodium Thioglycolate |
| 2.5 g | $KH_2PO_4$ |
| 7.5 g | $Na_2HPO_4$ |
| 0.5 g | Chicken Fat |
| 1.5 | Tween 80 |
| 5.0 g | Mannitol |

The culture medium was prepared:

I. A. Add tryptic soy broth, yeast extract, pyruvate and thioglycolate in proportional amounts to suitable number of rolling bottles. Add 15–20 porcelain balls to (each) bottle.

B. Place the bottles on a rolling mill and process or roll bottles for 8–24 hr.

II. Add proportional amounts of $KH_2PO_4$ and $Na_2HPO_4$ into separate roller bottles. Add 7–10 porcelain balls to each roller bottle. Process or roll for 3–5 hr.

III. A. Mix chicken fat and Tween 80 together.

B. Add proportional amounts of chicken fat/Tween 80 mix to roller bottles in Section II above after their initial process; i.e., after II rolled 3–5 hr.

C. Add proportional amounts of mannitol to roller bottles in Section II.

D. Process roller bottles of II, each having proportional amounts of the Tween 80 or chicken fat mix and mannitol, on rolling mill for 1–2 hr.

IV. A. Add contents of roller bottles in Section III to bottles in Section I.

B. Place bottles on rolling mill and process for 4–8 hr.

V. A. Combine contents of all roller bottles in Section IV into one large roller vessel.

B. Process on a roller mill till contents are mixed thoroughly.

For each section rolling times are approximate. It is important that all of the ingredients are uniformly dispersed throughout the blend at each stage. Inert or magnetic markers may be used to measure and assure uniform distribution.

The bottles (4,000 ml) are the typical ball mill bottles that are familiar in the powder processing industry. Any plastic bottle or equivalent that is not abraded by porcelain milling balls or the like and does not effect product performance can be used.

Alternatively, mixing of ingredients in the same order may be accomplished by any means that is commercially viable, such as fluid bed granulation, which distributes solvent based regent over the dry powder reagent or particles uniformly.

It is intended that the foregoing description be only illustrative of the present invention and that the present invention be limited only by the hereinafter appended claims.

We claim:

1. A heterogeneous dry powdered culture medium for repair of injured microbial cells which comprises a powdered mixture of:

(A) a first milled mixture of a nutrient medium for the microbial cells, yeast extract as a yeast derivative, pyruvate and thioglycolate as antioxidants, potassium dihydrogen phosphate, and sodium hydrogen phosphate as buffering salts, which forms a dry powder; and (B) a second milled mixture of chicken fat, polyoxyethylene sorbitan monooleate (TWEEN 80) as an emulsifier for the chicken fat, and mannitol as a carbon source for the microbial cells, which forms a dry powder, wherein each of the ingredients is present in amounts which promote the repair, wherein the first and second milled mixtures are mixed together to form the dry powdered culture medium.

2. The culture medium of claim 1 wherein the nutrient medium is present in an amount between 1 and 90 parts per part by weight of (A) together; the yeast derivative is between about 1 and 50 parts by weight part of (A) together; the buffering salts are present in an amount between about 1 and 90 parts by weight per part of (A) together; the chicken fat is present in an amount between about 0.1 and 50 parts by weight per part of (B) together; the TWEEN 80 is present in an amount between 0.1 and 50 parts by weight per part of (B) together; and the mannitol is present in an amount between about 1 and 90 parts by weight per part of B together.

3. A method for repairing injured microbial cells which comprises:

(a) providing a heterogeneous dry powdered culture medium for the repair of microbial cells which comprises as a powdered mixture:

(A) a first milled mixture of a nutrient medium for the microbial cells, yeast extract as a yeast derivative, pyruvate and thioglycolate as antioxidants, potassium dihydrogen phosphate and sodium hydrogen phosphate as buffering salts, which forms a dry powder; and (B) a second milled mixture of chicken fat, TWEEN 80 as an emulsifier, and mannitol as a carbon source for the microbial cells, which forms a dry powder, wherein each of the ingredients is present in amounts which promote the repair, wherein the first and second milled mixtures are mixed together to form the dry powdered culture medium;

(b) mixing the dry powdered culture medium with water to provide a liquid culture medium;

(c) providing the microbial cells in the liquid culture medium; and (d) culturing the cells in the liquid culture medium until the cells are repaired.

4. The method of claim 3 wherein the nutrient medium is present in an amount between 1 and 90 parts by weight per part of (A) together; the yeast derivative is between about 1 and 50 parts by weight per part of (A) together; the buffering salts are present in an amount between about 1 and 90 parts by weight per part of (A) together; the chicken fat is present in an amount between about 0.1 and 50 parts by weight per part of (B) together; the TWEEN 80 is present in an amount between 0.1 and 50 parts by weight per part of (B) together; and the mannitol is present in an amount between about 1 and 90 parts by weight per part of B together.

5. A method for preparing a heterogenous dry powdered culture medium for injured microbial cells which comprises:

(a) mixing a powdered mixture of:

(A) a first milled mixture of a nutrient medium for the microbial cells, yeast extract as a yeast derivative, pyruvate and thioglycolate as antioxidants, potassium dihydrogen phosphate and sodium hydrogen phosphate as buffering salts, which forms a dry powder; and (B) a second milled mixture of chicken fat, TWEEN 80 as an emulsifier for the chicken fat, and mannitol as a carbon source for the microbial cells, which forms a dry powder, wherein each of the ingredients is present in amounts which promote the repair, wherein the first and second milled mixtures are mixed together to form the dry powdered culture medium; and (b) packaging the dry powdered culture medium.

6. The method of claim 5 wherein the nutrient medium is present in an amount between 1 and 90 parts by weight per part of (A) together; the yeast derivative is between about 1 and 50 per parts by weight of (A) together; the buffering salts are present in an amount between about 1 and 90 parts by weight per part of (A) together; the chicken fat is present in an amount between about 0.1 and 50 parts by weight per part of (B) together; the TWEEN 80 is present in an amount between 0.1 and 50 parts by weight per part of (B) together; and the mannitol is present in an amount between about 1 and 90 parts by weight per part of B together.

\* \* \* \* \*

UNITED STATES PATENT AND TRADEMARK OFFICE
CERTIFICATE OF CORRECTION

PATENT NO. : 5,773,279
DATED : June 30, 1998
INVENTOR(S) : Raymond L. Miller, Martin R. Gould and Sudhakar Vulimiri It is certified that error appears in the above-identified patent and that said Letters Patent is hereby corrected as shown below:

Column 4, Table 1, line 6, "0005" should be --0.005--.

Column 4, Table 1, line 7, "005" should be --0.05--.

Signed and Sealed this

Twenty-ninth Day of September, 1998

Attest:

BRUCE LEHMAN

Attesting Officer      Commissioner of Patents and Trademarks